US010724953B2

(12) United States Patent
Zhang et al.

(10) Patent No.: US 10,724,953 B2
(45) Date of Patent: Jul. 28, 2020

(54) METHOD FOR EVALUATING PHAGOCYTIC CAPACITY AND FLUORESCENCE MEASUREMENT METHOD

(71) Applicant: HAMAMATSU PHOTONICS K.K., Hamamatsu-shi, Shizuoka (JP)

(72) Inventors: Ran Zhang, Takamatsu (JP); Hiroyuki Inagawa, Takamatsu (JP); Gen-Ichiro Soma, Tokyo (JP); Kimiko Kazumura, Hamamatsu (JP); Hiroshi Tsuchiya, Hamamatsu (JP); Naokazu Morishita, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 264 days.

(21) Appl. No.: 15/292,453

(22) Filed: Oct. 13, 2016

(65) Prior Publication Data

US 2017/0108436 A1    Apr. 20, 2017

(30) Foreign Application Priority Data

Oct. 15, 2015    (JP) .................................. 2015-203488

(51) Int. Cl.
*G01N 21/64* (2006.01)
*G01N 33/49* (2006.01)

(52) U.S. Cl.
CPC ..... *G01N 21/6428* (2013.01); *G01N 21/6408* (2013.01); *G01N 33/49* (2013.01); *G01N 2021/6439* (2013.01); *G01N 2201/062* (2013.01)

(58) Field of Classification Search
None
See application file for complete search history.

(56) References Cited

FOREIGN PATENT DOCUMENTS

| CN | 101846626 A | 9/2010 |
|---|---|---|
| CN | 102037359 A | 4/2011 |
| CN | 102262079 A | 11/2011 |
| CN | 102533646 A | 7/2012 |
| CN | 103267752 A | 8/2013 |
| CN | 104807797 A | 7/2015 |
| JP | 2010-508295 A | 3/2010 |
| JP | 2012-073109 A | 4/2012 |
| WO | WO-2008/076524 A2 | 6/2008 |

OTHER PUBLICATIONS

Zhang et al., Development of an Evaluation Device for Phagocytic Activity of New Phagocytes Using Simple and pH-sensitive Particles that Do Not Require Pre-treatment, Anticancer Research 36: 3613-3618 (2016).*
Schreiner et al., Phagocytosis and digestion of pH-sensitive fluorescent dye (Eos-FP) transfected *E. coli* in whole blood assays from patients with severe sepsis and septic shock, J. Cell Commun. Signal. (2011) 5:135-144.*
Wan et al., A rapid and simple microfluorometric phagocytosis assay, Journal ofImmunological Methods, 162 (1993) 1-7.*
MP-probes, Invitrogen Manual, May 2013.*
CBQCA, CBQCA protein quantification kit, Molecular Probes, Product Information, Oct. 11, 2011.*
Kyoko Yamazaki et al., "The measurement and evaluation of phagocytosis activity and ROS production in neutrophils using flow cytometry method," Japanese Journal of Hygiene, 2001, p. 351, vo. 56, No. 1 (including partial English translation).
Shoji Nagata, "Stress-Induced Immune Changes, and Brain-Immune Interaction," Journal of UOEH, 1993, pp. 161-171, vol. 15, No. 2 (including partial English translation).
Carol Góis Leandro et al., "Stress-Induced Downregulation of Macrophage Phagocytic Function Is Attenuated by Exercise Training in Rats," Neuroimmunomodulation, 2007, pp. 4-7, vol. 14, No. 1.
Anna C. Hearps et al., "HIV infection induces age-related changes to monocytes and innate immune activation in young men that persist despite combination antiretroviral therapy," AIDS, 2012, pp. 843-853, vol. 26, No. 7.
Brian J. Backskai et al., "Imaging of amyloid-β deposits in brains of living mice permits direct observation of clearance of plaques with immunotherapy," Nature Medicine, 2001, pp. 369-372, vol. 7, No. 3.
G. Jean Harry, Microglia during development and aging, Pharmacology & Therapeutics, 2013, pp. 313-326, vol. 139, No. 3.
Peter Mancuso et al., "Evaluation of phagocytosis and arachidonate metabolism by alveolar macrophages and recruited neutrophils from F344xBN rats of difference ages," Mechanisms of Ageing and Development, 2001, pp. 1899-1913, vol. 122, No. 15.
Mari E. Swift et al., "Age-Related Alterations in the Inflammatory Response to Dermal Injury," Journal of Investigative Dermatology, 2001, pp. 1027-1035, vol. 117, No. 5.

* cited by examiner

*Primary Examiner* — Blaine Lankford
(74) *Attorney, Agent, or Firm* — Faegre Drinker Biddle & Reath LLP

(57)    ABSTRACT

The present invention relates to a method for evaluating phagocytic capacity of phagocytes, including incorporating a fluorescent substance into phagocytes in a sample containing whole blood to obtain a measurement sample, standing the measurement sample for 2 minutes or more, measuring the fluorescence of the fluorescent substance, and evaluating the phagocytic capacity of phagocytes based on the intensity of the measured fluorescence, in which the measuring the fluorescence of the fluorescent substance includes irradiating an intermediate region of gravity direction of a placed measurement sample with an excitation light, and detecting the fluorescence generated from the fluorescent substance by the excitation light.

9 Claims, 3 Drawing Sheets

METHOD FOR EVALUATING PHAGOCYTIC CAPACITY AND FLUORESCENCE MEASUREMENT METHOD

CROSS-REFERENCE TO RELATED APPLICATION

This application claims priority to Japanese patent application No. 2015-203488 filed on Oct. 15, 2015, which is hereby incorporated by reference in its entirety.

TECHNICAL FIELD

The present invention relates to a method for evaluating phagocytic capacity and a fluorescence measurement method.

BACKGROUND

Phagocytosis (phagocytic action) is cellular endocytosis (intracellular incorporation) which acts not only against exogenous foreign substances such as bacteria, viruses, and dusts, but also acts against foreign substances that occur in the living body (unwanted substances), such as dead cells, oxidized LDL, and denatured proteins. Elimination of foreign substances by phagocytes such as macrophages and neutrophils plays an important role in the homeostatic maintenance, On the other hand, there is known a decrease in homeostatic function due to a decline of phagocytic capacity. For example, there are a report that delay of wound healing due to aging is correlated with a decreased phagocytic function of macrophages infiltrating into wound areas (Journal of Investigative Dermatology, 2001, Vol. 117, pp. 1027 to 1035), a report that in bacterial pneumonia due to aging, a decrease in the phagocytic capacity of migrating neutrophils is associated with susceptibility to infections (Mechanisms of Ageing and Development, 2001, Vol. 122, pp. 1899 to 1913), a report showing a decrease in amyloid-β phagocytosis of brain phagocytes (microglia) with aging (Pharmacology & Therapeutics, 2013, Vol. 139, pp. 313 to 326), a report that an elimination of amyloid-β is increased by enhanced microglial phagocytosis (Nature Medicine, 2001, Vol. 7, pp. 369 to 372), and the like. Based on these reports, an ability of phagocytes to eliminate foreign substances (phagocytic capacity) may serve as an indicator for facilitation of wound healing, an ability to prevent against infections, maintenance of brain function, or the like. It has been reported that phagocytic capacity of phagocytes (monocytes) in human peripheral blood is decreased with aging (AIDS, 2012, Vol. 26, pp. 843 to 853). Further, it is known that phagocytosis is decreased due to stress (Journal of UOEH, 1993, Vol. 15, pp. 161 to 171 and Neuroimmunomodulation, 2007, Vol. 14, pp. 4 to 7). Taken together the foregoing, it can be considered that it is useful to measure and evaluate phagocytic capacity of peripheral blood as an indicator of health status.

As a method for evaluating phagocytic capacity of phagocytes, for example, there are known a method of uptaking fluorescent latex beads into phagocytes and counting cells which have incorporated fluorescent latex beads under a fluorescent microscope, and a method of incorporating fluorescent latex beads into phagocytes and analyzing bead-incorporated cells using a flow cytometer (for example, Japanese Journal of Hygiene, April 2001, Vol. 56, No. 1, p. 315).

SUMMARY

Decrease of phagocytic capacity results in being readily susceptible to infectious diseases and also has been pointed out to have the correlation with a large number of diseases such as an increase of kidney stones, worsening of Alzheimer's disease, lowering of muscle regeneration, and pulmonary alveolar proteinosis. Further, phagocytic capacity has also been found to decline with aging, and therefore a capable system of conveniently evaluating phagocytic capacity at the individual level is necessary in order to achieve a healthy longevity society in Japan which has entered a super-aged society.

With a conventional method for evaluating phagocytic capacity using a fluorescent microscope or a flow cytometer, measurements cannot be carried out in samples containing red blood cells or the like and therefore it is necessary to separate phagocytes. The separation of phagocytes requires a complicated operation.

An object of the present invention is to provide a method which can evaluate phagocytic capacity of phagocytes using a sample containing whole blood, without requiring a complicated operation.

The present invention relates to a method for evaluating phagocytic capacity of phagocytes. The method for evaluating phagocytic capacity according to the present invention includes incorporating a fluorescent substance into phagocytes in a sample containing whole blood to obtain a measurement sample, standing the measurement sample for 2 minutes or more,
measuring the fluorescence of the fluorescent substance, and
evaluating the phagocytic capacity of phagocytes based on the intensity of the measured fluorescence, in which the measuring the fluorescence of the fluorescent substance includes irradiating an intermediate region of gravity direction of a placed measurement sample with an excitation light, and detecting the fluorescence generated from the fluorescent substance by the excitation light.

The method for evaluating phagocytic capacity according to the present invention can evaluate phagocytic capacity of phagocytes using a sample containing whole blood without requiring a complicated operation such as blood cell separation, because an intermediate region of gravity direction of a placed measurement sample is irradiated with an excitation light to detect fluorescence after a measurement sample is allowed to stand for 2 minutes or more. By standing a measurement sample for 2 minutes or more prior to the measurement of fluorescence, transparency of the measurement sample is improved, whereby detection of weak fluorescence becomes possible. Further, by irradiating an intermediate region of gravity direction of a placed measurement sample with an excitation light, it becomes possible to more accurately measure the intensity of fluorescence from the fluorescent substance phagocytosed by phagocytes.

With respect to the above-mentioned method for evaluating phagocytic capacity, incorporation of the fluorescent substance into phagocytes is preferably carried out for 120 minutes or more. As a result, it is possible to more conveniently evaluate a maximum phagocytic capacity of phagocytes because the phagocytosis by phagocytes is saturated.

The above-mentioned method for evaluating phagocytic capacity preferably further includes mixing the measurement sample, prior to standing the measurement sample. Thus, it is possible to more accurately measure the fluorescence from the fluorescent substance phagocytosed by phagocytes.

Since a required sample amount (blood volume) may be a trace amount in the above-mentioned method for evaluating phagocytic capacity, the amount of the whole blood contained in the measurement sample may be 0.5 to 10 µL. Such a trace amount of blood (whole blood) may be collected, for example, with a low-pain self-blood collection device (lancet) which is used by a diabetic patient for assessment of a daily glucose level. In other words, blood sampling by a medical personnel is not required, so the phagocytic capacity can be conveniently evaluated at the individual level.

The present invention can also be regarded as a fluorescence measurement method for measuring fluorescence of a fluorescent substance incorporated into cells, using a sample containing whole blood. The fluorescence measurement method according to the present invention includes incorporating a fluorescent substance into cells in a sample containing whole blood to obtain a measurement sample, standing the measurement sample for 2 minutes or more, and measuring the fluorescence of the fluorescent substance, in which the measuring the fluorescence of the fluorescent substance includes irradiating an intermediate region of gravity direction of a placed measurement sample with an excitation light, and detecting the fluorescence generated from the fluorescent substance by the excitation light.

The above-mentioned fluorescence measurement method preferably further includes mixing the measurement sample, prior to standing the measurement sample.

According to the present invention, it becomes possible to provide a method which can evaluate phagocytic capacity of phagocytes using a sample containing whole blood, without requiring a complicated operation such as separation of phagocytes from blood.

DETAILED DESCRIPTION

Figure 1:
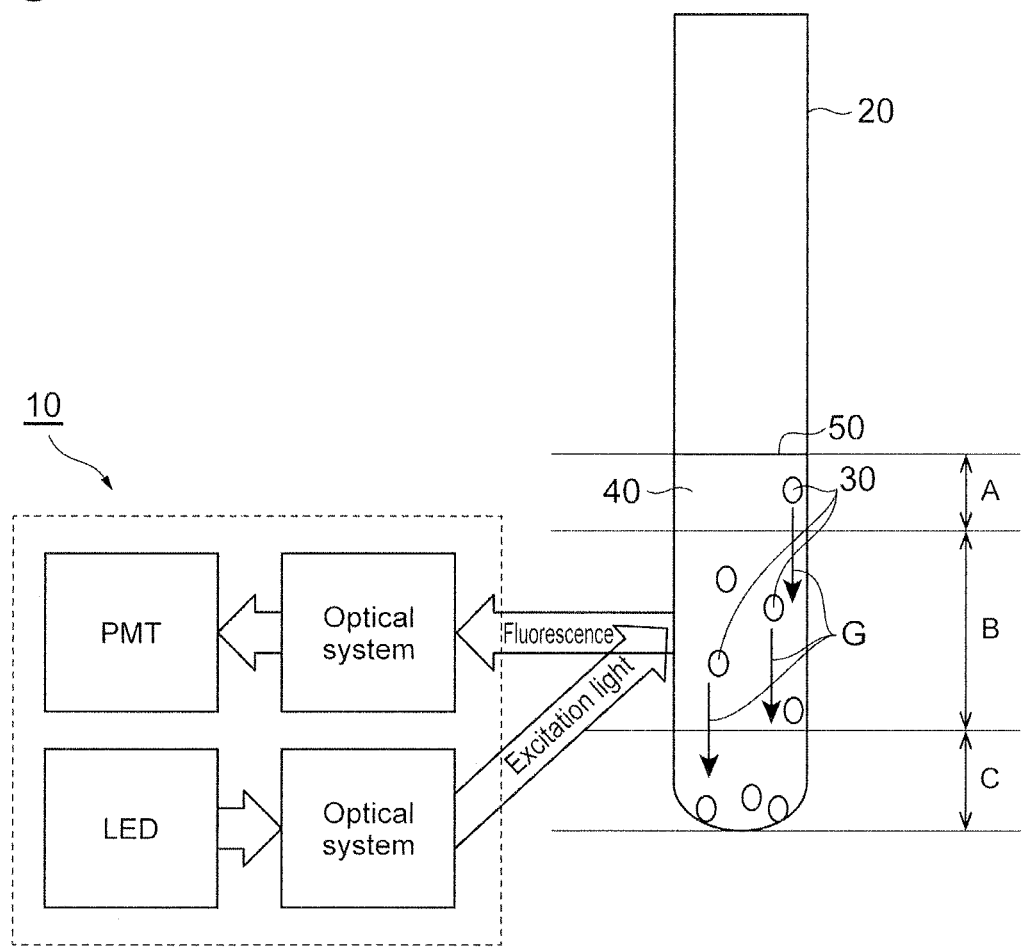
FIG. 1 is an explanatory diagram showing one embodiment of a fluorescence measurement method of a fluorescent substance incorporated into cells.

Hereinafter, embodiments of the present invention will be described in detail with reference to the accompanying drawings where appropriate. However, the present invention is not limited to the following embodiments. It should be noted that, in the drawings, the same or corresponding parts are denoted by the same reference numerals, and redundant description thereof will be omitted as appropriate.

The method for evaluating phagocytic capacity of phagocytes according to the present embodiment includes a step of incorporating a fluorescent substance into phagocytes in a sample containing whole blood to obtain a measurement sample (hereinafter, also referred to as "preparation step"), a step of standing the measurement sample for 2 minutes or more (hereinafter, also referred to as "standing step"), a step of measuring the fluorescence of the fluorescent substance (hereinafter, also referred to as "fluorescence measuring step"), and a step of evaluating the phagocytic capacity of phagocytes based on the intensity of the measured fluorescence (hereinafter, also referred to as "evaluation step").

Phagocytes are cells responsible for a phagocytic action involving intracellular incorporation of foreign substances by endocytosis (phagocytosis), intracellular decomposition of such foreign substances, or the like. The term "phagocytic capacity of phagocytes" refers to capability of a phagocytic action (that is, an ability to eliminate foreign substances). Examples of foreign substances include exogenous foreign substances such as bacteria, viruses and dusts, and foreign substances that occur in the living body (unwanted substances), such as dead cells, oxidized LDL and denatured proteins. Specific examples of phagocytes include macrophages, monocytes, neutrophils, and dendritic cells.

The preparation step is a step of incorporating a fluorescent substance into phagocytes in a sample containing whole blood to obtain a measurement sample. In the method for evaluating phagocytic capacity according to the present embodiment, it is possible to evaluate the phagocytic capacity using a sample containing whole blood, since there is no need to separate phagocytes from blood.

The sample containing whole blood may be whole blood itself, or may also be a sample obtained by diluting whole blood. The dilution of whole blood may employ, for example, common physiological isotonic buffer such as saline, phosphate buffered saline (PBS), a Hank's balanced salt solution, Tris-buffered saline, or Hepes buffer solution. A dilution ratio in the case of diluting whole blood is not particularly limited, and may be appropriately set depending on the purpose. The dilution ratio is preferably 10 to 2000-fold, and more preferably 100 to 1000-fold.

Although an amount of whole blood to be used is not particularly limited, the amount of whole blood contained in a measurement sample may be 0.5 to 10 µL, preferably 0.5 to 7.5 µL, and more preferably 0.5 to 5 µL since a required sample amount (blood volume) may be a trace amount in the method for evaluating phagocytic capacity according to the present embodiment.

The fluorescent substance is not particularly limited as long as it is phagocytosed by phagocytes. Fluorescent substances which have been conventionally used for the evaluation of phagocytic capacity of phagocytes may be preferably used. Specific examples of the fluorescent substance include fluorescent latex beads, and pH-sensitive fluorescent particles (for example, Green *E. coli* (manufactured by Molecular Probes, Inc.), and stained particles of Zymosan, *E. coli, Staphylococcus aureus*, or the like using a pH-sensitive fluorescent dye such as Acid Flow (Goryo Chemical, Inc.)). These fluorescent substances may be used alone or in combination of two or more thereof.

Incorporation of a fluorescent substance into phagocytes may be carried out according to a conventional method. More specifically, for example, a fluorescent substance can be incorporated into phagocytes by adding the fluorescent substance to a sample containing whole blood, and incubating the sample at a temperature of 25° C. to 37° C. for 30 minutes to 24 hours. The incubation time of 10 minutes or more can result in sufficient incorporation of a fluorescent substance into phagocytes. Further, by setting the incubation time to 120 minutes (2 hours) or more, the incorporation of a fluorescent substance into phagocytes is saturated, whereby it is possible to more conveniently evaluate a maximum phagocytic capacity of phagocytes.

The standing step is a step of standing a measurement sample for 2 minutes or more. By standing the measurement sample for 2 minutes or more prior to the measurement of fluorescence, transparency of the measurement sample is improved even when using a sample containing whole blood, so it becomes possible to detect weak fluorescence.

With respect to the standing time of a measurement sample, about 1 minute may be effective. More suitably, the standing time is not particularly limited as long as it is 2 minutes or more. From the viewpoint of improving detection efficiency, the standing time is preferably 2 to 30 minutes, and more preferably 2 to 10 minutes.

The standing step is preferably carried out by standing a measurement sample in a state of being housed in a measurement container for 2 minutes or more, and more preferably by standing a measurement sample in a state of being housed in a measurement container which is in a state of being further set in a fluorescence measurement apparatus, for 2 minutes or more. Thus, detection sensitivity for weak fluorescence is further improved.

In one embodiment, it is preferred to further include a step of mixing a measurement sample (hereinafter, also referred to as "mixing step") prior to the standing step. By including the mixing step, the fluorescence from the fluorescent substance phagocytosed by phagocytes can be more accurately measured. The mixing step may be carried out, for example, by a method of inverting up and down a container containing a measurement sample, a method of stirring a measurement sample, or the like.

The fluorescence measuring step is a step of measuring the fluorescence of a fluorescent substance, using a measurement sample which was allowed to stand for 2 minutes or more in the standing step. The fluorescence measuring step includes irradiating an intermediate region of gravity direction of a placed measurement sample with an excitation light, and detecting the fluorescence generated from the fluorescent substance by the excitation light. The fluorescence measuring step is preferably carried out immediately after the standing step.

The excitation light is irradiated on an intermediate region of gravity direction of a placed measurement sample. As used herein, the "intermediate region of gravity direction" refers to a third region to be described below, when a measurement sample is divided into a first region (upper region) including a gas-liquid interface, a second region (lower region) including a bottom surface of a measurement container where a measurement sample is housed, and a third region between the first region and the second region, along the gravity direction of a placed measurement sample.

FIG. 1 is an explanatory diagram showing one embodiment of a fluorescence measurement method of a fluorescent substance incorporated into cells. As shown in FIG. 1, the measurement of fluorescence is carried out by irradiating a measurement sample 40 containing phagocytes 30 having the incorporation of a fluorescent substance with an excitation light from a fluorescence measurement apparatus 10, and detecting the resulting fluorescence by the fluorescence measurement apparatus 10. The measurement sample 40 is usually housed in a measurement container 20 that can be placed on a sample part of the fluorescence measurement apparatus 10.

As shown in FIG. 1, a third region B is irradiated with an excitation light, when the measurement sample 40 is divided into a first region A including a gas-liquid interface 50, a second region C including the bottom surface of the measurement container 20, and a third region (intermediate region) B between the first region A and the second region C, along the gravity direction of the measurement sample 40. By irradiating the third region B with an excitation light, it becomes possible to more accurately measure the intensity of fluorescence from a fluorescent substance phagocytosed by phagocytes. In other words, cells contained in whole blood, including phagocytes 30 having an incorporation of a fluorescent substance, are slowly precipitated in the direction of gravity (in FIG. 1, direction of G). At this time, the number of fluorescent substances phagocytosed by phagocytes also becomes balanced in the third region B which is an intermediate region, since a balance is made between the number of cells entering the third region B from the first region A, and the number of cells advancing to the second region C from the third region B. Therefore, it becomes possible to more accurately measure the intensity of fluorescence. Further, regarding the first region A, scattering of light (excitation light and fluorescence) is likely to occur in the gas-liquid interface, and regarding the second region C, scattering of light (excitation light and fluorescence) is likely to occur in the bottom surface of a measurement container, whereas such scattering is less likely to occur in the third region B, which is a factor by which accurate measurement becomes possible.

The "intermediate region of gravity direction" may be, for example, a region between the uppermost region and the lowermost region, when a measurement sample is equally divided into n numbers of regions along the gravity direction of a placed measurement sample. Here, n is a natural number of 3 to 10. For example, when n is 10, the "intermediate region of gravity direction" is $2^{nd}$ to $9^{th}$ regions when divided regions are numbered as $1^{st}$ to $10^{th}$ regions in order from the uppermost end to the lowermost end. Further, the "intermediate region of gravity direction" may be a substantially central portion of the gravity direction of a placed measurement sample.

As the measurement container and the fluorescence measurement apparatus, existing measurement containers and measurement apparatuses used for the measurement of fluorescence may be used without particular limitation.

The evaluation step is a step of evaluating phagocytic capacity of phagocytes, based on the intensity of the measured fluorescence. Higher intensity of the measured fluorescence represents a greater amount of a fluorescent substance phagocytosed by phagocytes. That is, higher intensity of the measured fluorescence is evaluated as having higher phagocytic capacity.

In the evaluation step, the phagocytic capacity of phagocytes may be evaluated based on the value obtained by correcting control fluorescence intensity from the intensity of the measured fluorescence. Here, the control fluorescence intensity is a value obtained by measuring the intensity of fluorescence in the same manner as in the preparation step, for example, using a sample obtained immediately after mixing a sample containing whole blood and a fluorescent substance in the preparation step (that is, a sample at a point of time where phagocytes did not phagocytose a fluorescent substance or phagocytosed only a slight amount of a fluorescent substance). How to set the control fluorescence intensity may be appropriately set depending on the purpose of correction.

With the method for evaluating phagocytic capacity of phagocytes according to the present embodiment, it becomes possible to measure the fluorescence with good sensitivity from a fluorescent substance incorporated into cells even in a sample containing whole blood, by standing a measurement sample for 2 minutes or more in the standing step, and irradiating an intermediate region of gravity direction of a placed measurement container with an excitation light in the fluorescence measuring step. Accordingly, the present invention can also be regarded as a fluorescence measurement method for measuring fluorescence of a fluorescent substance incorporated into cells, using a sample containing whole blood.

The fluorescence measurement method according to the present embodiment includes a step of incorporating a fluorescent substance into cells in a sample containing whole blood to obtain a measurement sample (preparation step), a step of standing the measurement sample for 2 minutes or more (standing step), and a step of measuring the fluorescence of the fluorescent substance (fluorescence measuring step).

A specific embodiment, a preferred embodiment, or the like of individual steps in the fluorescence measurement method according to the present embodiment is as described in the method for evaluating phagocytic capacity.

EXAMPLES

Hereinafter, the present invention will be described more specifically with reference to the following Examples. However, the present invention is not limited thereto.

[Evaluation of Phagocytic Capacity of Phagocytes]

Phosphate buffered saline (PBS) containing 0.2 w/v % of pH-sensitive fluorescent particles (Green *E. coli*, manufactured by Molecular Probes, Inc.) was placed in a microtube and maintained at 37° C. Then, 3 µL of human peripheral blood collected with a lancet was added thereto, and the microtube was slowly inverted up and down several times to mix the contents therein. Then, after standing for 2 minutes at 37° C., the microtube was set in a fluorescence measurement apparatus having an optical system shown in FIG. 1, and fluorescence was measured. The fluorescence was measured for about 10 seconds, and an average value of the measured values was calculated (control fluorescence intensity).

Next, the microtube was incubated for a predetermined time (60 minutes, 80 minutes, 120 minutes, or 180 minutes) at 37° C. such that pH-sensitive fluorescent particles were phagocytosed by phagocytes, and then the microtube was slowly inverted up and down several times to mix the contents therein. This was followed by standing for 2 minutes at 37° C., and fluorescence was measured as in the control fluorescence intensity. A value obtained by subtracting the control fluorescence intensity from the resulting measured value (average value) is shown in FIG. 2.

Figure 2:
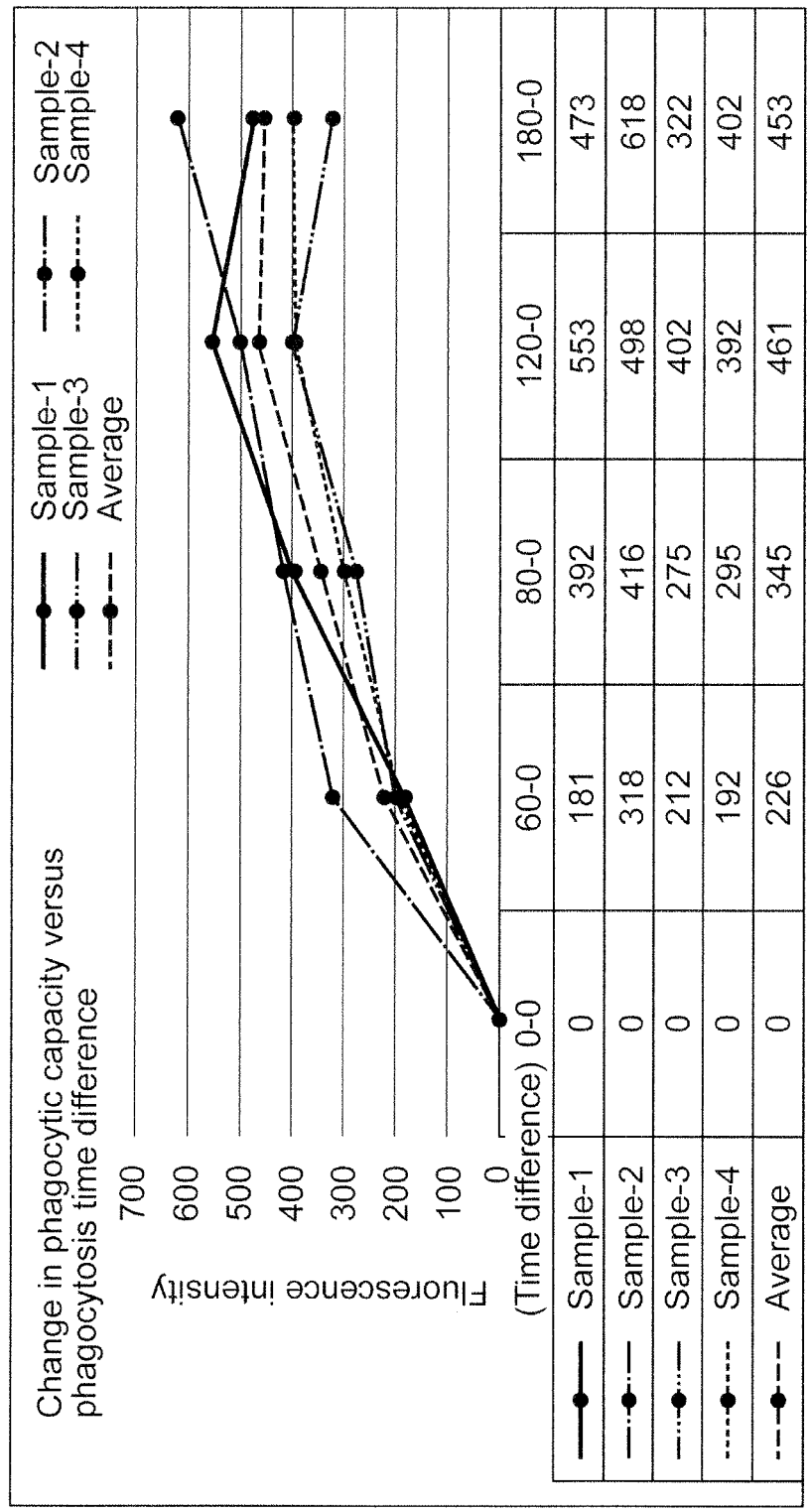
FIG. 2 is a graph showing the evaluation results of phagocytic capacity versus a phagocytosis time.

As shown in FIG. 2, it can be seen that the phagocytosis is in progress since the fluorescence intensity is increased until a phagocytosis time of 120 minutes. Further, it can be seen that phagocytosis is saturated at a phagocytosis time of 120 minutes or more, since there is no significant difference in the fluorescence intensity between a phagocytosis time of 120 minutes and a phagocytosis time of 180 minutes. From these results, it became clear that the value measured within a phagocytosis time of 120 minutes can be evaluated as the phagocytic capacity of phagocytes. Further, it became clear that the measured value at a phagocytosis time of 120 minutes (or 120 minutes or more) can be evaluated as the maximum phagocytic capacity of phagocytes since phagocytosis is saturated.

[Measurement of Fluorescence of Intracellular Fluorescent Substance]

Phosphate buffered saline (PBS) containing 0.2 w/v % of pH-sensitive fluorescent particles (Green *E. coli*) was placed in a microtube and maintained at 37° C. Then, 3 µL of human peripheral blood collected with a lancet was added thereto, and the microtube was slowly inverted up and down several times to mix the contents therein. Then, after standing for a predetermined time (0 minutes, 1 minute, 2 minutes, 3 minutes, 4 minutes, or 5 minutes) at 37° C., the microtube was set in a fluorescence measurement apparatus having an optical system shown in FIG. 1, and fluorescence was measured. The fluorescence was measured for about 10 seconds, and an average value of the measured values was calculated.

Figure 3:
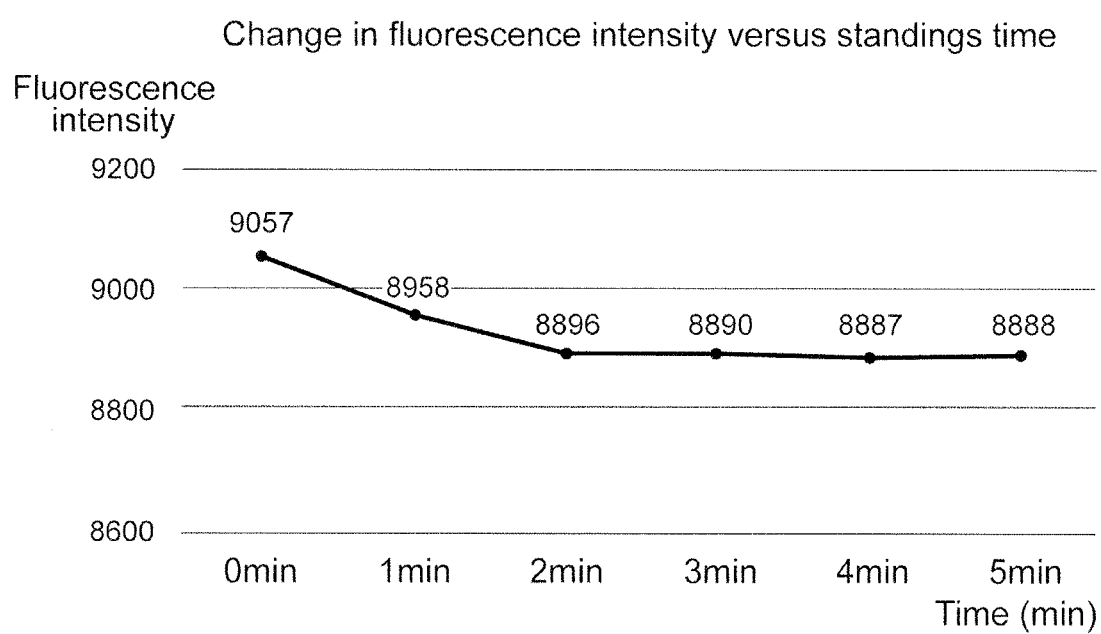
FIG. 3 is a graph showing a change in fluorescence intensity versus standings time prior to the measurement of fluorescence.

The results are shown in FIG. 3. It became clear that the measured value of fluorescence was stable by taking 2 minutes or more of standing time prior to the measurement of fluorescence. In other words, the fluorescence from the pH-sensitive fluorescent particles phagocytosed by phagocytes can be accurately measured by taking 2 minutes or more of standing time prior to the measurement of fluorescence.

SYMBOLS

10 . . . fluorescence measurement apparatus, 20 . . . measurement container, 30 . . . phagocytes having the incorporation of a fluorescent substance, 40 . . . measurement sample, 50 . . . gas-liquid interface, A . . . first region, B . . . third region (intermediate region), C . . . second region, G . . . direction of gravity.

What is claimed is:

1. A method for evaluating phagocytic capacity of phagocytes, comprising:
   incorporating a fluorescent substance into phagocytes in a sample containing whole blood including red blood cells to obtain a measurement sample,
   leaving to stand the measurement sample for 2 minutes or more,
   measuring the fluorescence of the fluorescent substance in the measurement sample containing whole blood including red blood cells, and
   evaluating the phagocytic capacity of phagocytes based on the intensity of the measured fluorescence,
   wherein the measuring the fluorescence of the fluorescent substance includes irradiating an intermediate region in the direction of gravity of a placed measurement sample with an excitation light, and detecting the fluorescence generated from the fluorescent substance by the excitation light.

2. The method for evaluating phagocytic capacity according to claim 1, wherein incorporation of the fluorescent substance into phagocytes is carried out for 120 minutes or more.

3. The method for evaluating phagocytic capacity according to claim 1, further comprising:
   mixing the measurement sample, prior to leaving to stand the measurement sample.

4. The method for evaluating phagocytic capacity according to claim 2, further comprising:
   mixing the measurement sample, prior to leaving to stand the measurement sample.

5. The method for evaluating phagocytic capacity according to claim 1, wherein an amount of the whole blood contained in the measurement sample is 0.5 to 10 µL.

6. The method for evaluating phagocytic capacity according to claim 2, wherein an amount of the whole blood contained in the measurement sample is 0.5 to 10 µL.

7. The method for evaluating phagocytic capacity according to claim 3, wherein an amount of the whole blood contained in the measurement sample is 0.5 to 10 µL.

8. The method for evaluating phagocytic capacity according to claim 4, wherein an amount of the whole blood contained in the measurement sample is 0.5 to 10 µL.

9. The method for evaluating phagocytic capacity according to claim 1, wherein the whole blood includes red blood cells that are not lysed.

* * * * *